(12) United States Patent
Singh

(10) Patent No.: US 9,480,665 B2
(45) Date of Patent: Nov. 1, 2016

(54) METHODS OF TREATING PAIN OR FEVER USING PHARMACEUTICALLY ACTIVE ACETAMINOPHEN DIMERS LINKED THROUGH PHENOLIC HYDROXYL GROUPS

(71) Applicant: OrphoMed, Inc., Mill Valley, CA (US)

(72) Inventor: Nikhilesh Nihala Singh, Mill Valley, CA (US)

(73) Assignee: ORPHOMED, INC., Mill Valley, CA (US)

( * ) Notice: Subject to any disclaimer, the term of this patent is extended or adjusted under 35 U.S.C. 154(b) by 0 days.

(21) Appl. No.: 14/922,362

(22) Filed: Oct. 26, 2015

(65) Prior Publication Data

US 2016/0045462 A1 Feb. 18, 2016

Related U.S. Application Data

(63) Continuation-in-part of application No. 14/697,155, filed on Apr. 27, 2015, now Pat. No. 9,309,256.

(60) Provisional application No. 61/985,207, filed on Apr. 28, 2014, provisional application No. 62/101,768, filed on Jan. 9, 2015, provisional application No. 62/176,883, filed on Jan. 9, 2015.

(51) Int. Cl.
| | |
|---|---|
| *A61K 31/167* | (2006.01) |
| *A61K 31/16* | (2006.01) |
| *A61K 45/06* | (2006.01) |
| *A61K 9/20* | (2006.01) |
| *A61K 9/00* | (2006.01) |
| *A61K 31/137* | (2006.01) |
| *A61K 31/485* | (2006.01) |
| *C07C 217/64* | (2006.01) |
| *C07C 217/70* | (2006.01) |
| *C07C 233/25* | (2006.01) |
| *C07D 489/02* | (2006.01) |
| *C07D 489/08* | (2006.01) |
| *C07D 489/12* | (2006.01) |
| *C07D 519/00* | (2006.01) |

(52) U.S. Cl.
CPC .......... *A61K 31/167* (2013.01); *A61K 9/0053* (2013.01); *A61K 9/20* (2013.01); *A61K 31/137* (2013.01); *A61K 31/485* (2013.01); *A61K 45/06* (2013.01); *C07C 217/64* (2013.01); *C07C 217/70* (2013.01); *C07C 233/25* (2013.01); *C07D 489/02* (2013.01); *C07D 489/08* (2013.01); *C07D 489/12* (2013.01); *C07D 519/00* (2013.01); *C07C 2101/14* (2013.01)

(58) Field of Classification Search
USPC ................................................ 514/616, 629
See application file for complete search history.

(56) References Cited

U.S. PATENT DOCUMENTS

| | | | |
|---|---|---|---|
| 3,896,235 A | * | 7/1975 | Harfenist .............. C07C 233/12 514/616 |
| 7,759,358 B2 | | 7/2010 | Crooks et al. |
| 8,461,171 B2 | | 6/2013 | Holaday et al. |
| 8,617,530 B2 | | 12/2013 | Roberts et al. |
| 9,309,256 B2 | | 4/2016 | Singh |
| 9,321,780 B2 | | 4/2016 | Singh |

OTHER PUBLICATIONS

Kumar, R. et al.: Synthesis and evaluation of acetaminophen derivatives as analgesic, antipyretic and anti-inflammatory agents. Der Pharma Chemica, vol. 5, pp. 73-78, 2013.*
Andersson, David A. et al., "TRPA1 mediates spinal antinociception induced by acetaminophen and the cannabinoid $\Delta^9$-tetrahydrocannabiorcol," *Nature Communications* (Nov. 22, 2011); 11 pages.
Dunee (posted by) Mar. 6, 2012, "Difference Between Ester and Ether," http://www.differencebetween.com/difference-between-ester-and-vs-ether/: (downloaded Jun. 9, 2016); 5 pages.
Ganley, Charles et al. "Acetaminophen Overdose and Liver Injury—Background and Options for Reducing Injury;" *FDA Publication* (May 22, 2009) http://www.fda.gov/downloads/AdvisoryCommittees/CommitteesMeetingMaterials/Drugs/DrugSafetyandRiskManagementAdvisoryCommittee/UCM164897.pdf (downloaded 21 pages Jun. 2, 2016.).
Huttunen, Kristiina et al, Prodrugs—from Serendipity to Rational Design, *Pharmacological Reviews* (2011) 63:750-771; (downloaded from pharmrev.aspetjournals.org on Apr. 25, 2016).
Moyer, Ann M. et al., "Acetaminophen-NAPQI Hepatotoxicity: A Cell Line Model System Genome-Wide Associate Study," *Toxicological Sciences* (2011; Advance Access Publication Dec. 22, 2010); 120(1):33-41. (doi:10.1093/toxsci/kfq375).
NAPQI (definition) From Wikipedia, the free encyclopedia; https://en.wikipedia.org/wiki/NAPQI (downloaded Jun. 2, 2016); 4 pages.
Paracetamol (definition) From Wikipedia, the free encyclopedia; https://en.wikipedia.org/wiki/Paracetamol (downloaded Jun. 2, 2016); 12 pages.
Parang, Keykavous et al., Novel Approaches for Designing 5'-O'Ester Prodrugs of 3'-Azido-2'3'-Dideoxythymidine (AZT), *Chapman University; Chapman University Digital Commons; Pharmacy Faculty Articles and Research* (2000); http://digitalcommons.chapman.edu/cgi/viewcontent.cgi?article=1105&context=pharmacy_articles (downloaded Jun. 2, 2016).
Rumack, Barry H., M.D. et al., "Acetaminophen Poisoning and Toxicity," *Pediatrics* (Jun. 1, 1975); 55:871-876.
Wilkinson, Juliet, "Contraindications for Tylenol," *livestrong.com* http://www.livestrong.com/article/162564-contraindications-for-tylenol/ (Updated Nov. 29, 2015; downloaded Jun. 3, 2016); 2 pages.

* cited by examiner

*Primary Examiner* — Charanjit Aulakh
(74) *Attorney, Agent, or Firm* — Mintz, Levin, Cohn, Ferris, Glovsky and Popeo, P.C.

(57) ABSTRACT

Provided herein are methods for treating pain such as acute or chronic pain or fever in subject without risking hepatotoxicity. The subject may be at risk of hepatotoxicity if administrated an acetaminophen monomer. The method includes administering a pharmaceutical composition containing an acetaminophen dimer compound, wherein the phenolic hydroxyl groups of two acetaminophen compounds are linked via an ethylene spacer.

13 Claims, 3 Drawing Sheets

Synthesis of the Acetaminophen Dimer

Metabolic stability of acetaminophen dimer

Analgesic effect of acetaminophen dimer in comparison to the vehicle, morphine, ethylene glycol ether buprenorphine, and acetaminophen

METHODS OF TREATING PAIN OR FEVER USING PHARMACEUTICALLY ACTIVE ACETAMINOPHEN DIMERS LINKED THROUGH PHENOLIC HYDROXYL GROUPS

CROSS-REFERENCES TO RELATED APPLICATIONS

This application is a continuation-in-part of U.S. patent application Ser. No. 14/697,155 filed Apr. 27, 2015, which application claims the benefit of priority under 35, U.S.C. §119(e) of U.S. Provisional Application No. 61/985,207 filed Apr. 28, 2014; U.S. Provisional Application No. 62/101,768 filed Jan. 9, 2015; and U.S. Provisional Application No. 62/176,883 filed Jan. 9, 2015, each of which is herein incorporated by reference in its entirety for all purposes.

BACKGROUND OF THE INVENTION

Acetaminophen (Formula 1), chemically named N-acetyl-p-aminophenol, is one of the most widely used medications in the United States.

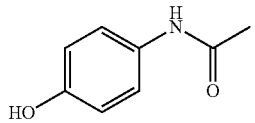

Formula 1

Acetaminophen is an over-the-counter analgesic and antipyretic, commonly sold under the trade name Tylenol®. Acetaminophen is classified as a mild analgesic. It is commonly used for the relief of headaches and other minor aches and pains and is a major ingredient in numerous cold and flu remedies. In combination with opioid analgesics such as codeine, oxycodone, and hydrocodone, acetaminophen can also be used in the management of more severe pain such as post-surgical pain and providing palliative care in advanced cancer patients.

When administered in proper therapeutic doses, acetaminophen is considered safe and harmless. Unfortunately, misuse and overdose of the drug can lead to hepatotoxicity and even, death.

Acetaminophen induced hepatotoxicity arises from impaired metabolism of acetaminophen monomers by the liver. Acetaminophen has a single phenolic hydroxyl group that confers photo instability and undergoes rapid pre-systemic metabolism (first-pass metabolism) in the liver, and to a lesser extent in the kidneys and intestine.

Acetaminophen (e.g., acetaminophen monomer) is metabolized via conjugation with sulfate or glucuronide to form sulfate esters or glucuronide esters. A small percentage of the drug (about 5%-10%) is oxidized by CYP450 enzymes (CYP2E1, 1A2, 2A6 and 3A4) to a hepatotoxic, reactive metabolite, N-acetyl-p-benzoquinone imine (NAPQI). NAPQI can be detoxified by rapid conjugation with glutathione, a sulfhydryl donor, and is eliminated in the urine or bile. However, if NAPQI is in excess or if glutathione stores are reduced, for example, by 70% compared to normal, NAPQI covalently binds to the cysteinyl sulfhydryl groups of proteins in the liver to form NAPQI-protein adducts. These NAPQI-protein adducts target mitochondrial proteins and ion channels of hepatocytes, leading to loss of energy production, ion misbalance, and cell death. As such, improper metabolism of acetaminophen can lead to hepatocellular damage, hepatic dysfunction, hepatic necrosis and organ failure.

Dosing recommendations have been established to minimize the risk of hepatotoxicity. According to current FDA guidelines for oral or rectal dosages of acetaminophen for treating pain, the maximum totally daily dose for adults is 3 g, with no more than 650 mg every 6 hours. For children under 12 years of age and/or less than 50 kg in weight, the maximum daily dose is 75 mg/kg, with a recommended dose of 10-15 mg/kg per dose every 4-6 hours but no more than 5 doses over a 24-hour period.

For intravenous dosing of adults and children equal or less than 50 kg in weight, the maximum total daily dose is 4 g, with no more than 1 g every 6 hours. For those less than 50 kg in weight, the maximum total daily dose is 75 mg/kg in 24 hours (up to 3750 mg), with no more than 15 mg/kg.

The minimum toxic dose of acetaminophen by oral administration is about 7.5 g to about 10 g for adults and about 150 mg/kg to about 200 mg/kg for children. Ingestion of more than 150 mg/kg or 12 g of acetaminophen by an adult is considered a toxic dose with a risk of developing hepatotoxicity. A comparable toxic dose for a child is more than 250-350 mg/kg.

Acetaminophen is not recommended for subjects who may develop hepatotoxicity upon receiving the drug. There is a need for an analgesic that has a lower likelihood of causing hepatotoxicity in a subject in need of pain relief.

BRIEF SUMMARY OF THE INVENTION

In one aspect, provided herein is a method of treating pain (acute or chronic pain) or fever in a patient having a risk of hepatotoxicity if administered an acetaminophen monomer. The method includes administering to the patient in need thereof a therapeutically effective amount of a pharmaceutical composition comprising a pharmaceutically acceptable carrier or excipient and an acetaminophen dimer compound having Formula (1):

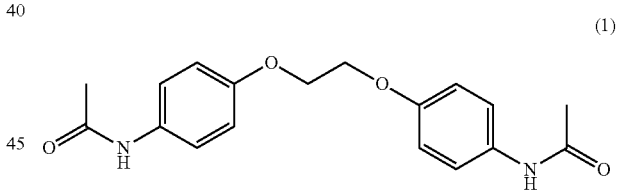

(1)

or a pharmaceutically acceptable salt or solvate thereof.

In some embodiments, the patient is an adult human patient. In other embodiments, the patient is a pediatric (i.e., infant, child or adolescent) human patient. A pediatric patient may be an individual from birth to up to 18-21 years of age. The patient may be experiencing a fever. Alternatively, the patient may suffer from pain (acute pain or chronic pain). In some embodiments, the patient is receiving treatment for cancer. In other embodiments, the patient suffers from gastrointestinal acidity or gastrointestinal reflux disease (GERD). The subject may be in need of palliative care.

The pharmaceutical composition can also include a barbiturate, opioid, antihistamine, caffeine, diphenhydramine, dextromethorphan, pseudoephedrine, biosimilar thereof, pharmaceutical equivalent thereof, or any combination thereof. In some embodiments, the pharmaceutical composition is administrated orally, rectally, sublingually, subcutaneously, intramuscularly, intravenously, transdermally, or transmucosally. The therapeutically effective amount administered may be about 500 mg to about 1000 mg. The pharmaceutical composition may be formulated as an oral tablet or extended release oral tablet.

In another aspect, provided herein is a method of treating pain (acute or chronic pain) or fever in a patient in need thereof without risking hepatotoxicity. The method includes administering to the patient a therapeutically effective amount of a pharmaceutical composition comprising a pharmaceutically acceptable carrier or excipient and an acetaminophen dimer compound having Formula (1):

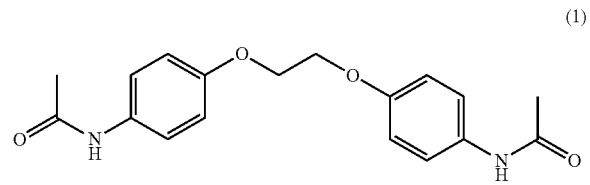 [SMILES: CC(=O)Nc1ccc(OCCOc2ccc(NC(C)=O)cc2)cc1]

(1)

or a pharmaceutically acceptable salt or solvate thereof.

In some embodiments, the patient is an adult human patient. In other embodiments, the patient is a pediatric (i.e., infant, child or adolescent) human patient. A pediatric patient may be an individual from birth to up to 18-21 years of age. The patient may be experiencing a fever. Alternatively, the patient may suffer from acute pain or chronic pain. In some embodiments, the patient is receiving treatment for cancer. In other embodiments, the patient suffers from gastrointestinal acidity or gastrointestinal reflux disease (GERD).

The pharmaceutical composition can also include a barbiturate, opioid, antihistamine, caffeine, diphenhydramine, dextromethorphan, pseudoephedrine, biosimilar thereof, pharmaceutical equivalent thereof, or any combination thereof. In some embodiments, the pharmaceutical composition is administered orally, rectally, sublingually, subcutaneously, intramuscularly, intravenously, transdermally, or transmucosally. The therapeutically effective amount administered may be about 500 mg to about 1000 mg. The pharmaceutical composition may be formulated as an oral tablet or extended release oral tablet.

The pharmaceutical composition provided herein can be used as a pain reliever, a fever reducer, sleep aid, antitussive, an analgesic, and/or a cough and cold aid. As such, the compositions can be administered to a subject, e.g., a human subject to treat pain such as acute pain or chronic pain, fever, a sleep disorder or problem, a cough, and/or a common cold.

Other objects, features, and advantages of the present invention will be apparent to one of skill in the art from the following detailed description and figures.

DETAILED DESCRIPTION OF THE INVENTION

I. Introduction

Figure 1:
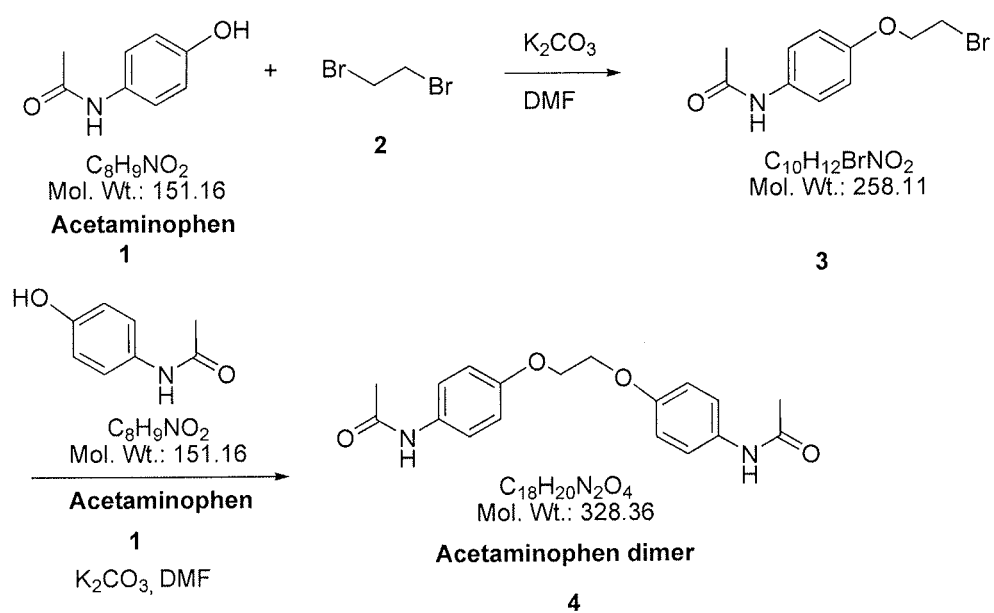
FIG. 1 provides a synthetic route to the acetaminophen dimer.

The present invention is based, in part, on the surprising discovery that dimerization of acetaminophen by O-alkylation through its phenolic hydroxyl group, such that the active agent residues are bridged by an ethylene linker, yields distinct advantages relative to the active acetaminophen monomer.

In opioids and other pharmaceutical agents characterized by a single phenolic hydroxyl group, the covalent linkage of two such agents via such groups by the ethylene linker yields homo-dimers which are essentially more resistant to pre-systemic metabolism than their parent molecules. The ethylene linkage is highly stable and in particular cases yields other distinct advantages as well.

The effect of dimerizing acetaminophen, according to the invention, is to prevent formation of the quinone metabolite of the parent compound, which is hepatotoxic in acute and chronic use. In addition, blocking the phenolic hydroxyl of the monomer, dimerization reduces the ionic nature of the active agent, potentially enhancing transport through the blood-brain barrier and hence, analgesia.

II. Definitions

When describing the compounds, compositions, methods and processes of this invention, the following terms have the following meanings, unless otherwise indicated.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The term "acute pain" refers to pain persisting for less than 3 to 6 months.

The term "chronic pain" refers to pain persisting for an extended period of time, for example, greater than three to 6 months, although the characteristic signs of pain can occur earlier or later than this period. Chronic pain may be mild, excruciating, episodic, or continuous.

The term "fever" refers to an elevated body temperature that is at or over about 37.7° C. (99.9° F.) for a human subject.

The term "infectious fever" refers a fever caused by or associated with an infectious cause, disorder or disease. Common causes of such fevers include upper and lower respiratory tract infections, gastrointestinal infections, urinary tract infection, and skin infections. Non-limiting pathogens associated with infectious diseases include viruses, bacteria, fungi, yeast, protozoans, nematodes, and other parasites.

The term "non-infectious fever" refers a fever caused by or associated with an inflammatory or neoplastic (cancer) disorder or disease. A non-infectious fever is not due to an infectious cause, disorder or disease. In some cases, a non-infectious fever is caused by a drug, an immunization, heat exhaustion, sunburn, and the like.

The term "therapeutically effective amount" refers to that amount of the therapeutic agent sufficient to ameliorate the targeted condition or symptoms. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

The term "treating," "treatment" and derivatives thereof to refers to the treating or treatment of a disease or medical condition (such as pain) in a patient, such as a mammal (particularly a human or an animal) which includes: ameliorating the disease or medical condition, i.e., eliminating or causing regression of the disease or medical condition in a patient; suppressing the disease or medical condition, i.e., slowing or arresting the development of the disease or medical condition in a patient; or alleviating the symptoms of the disease or medical condition in a patient. The term encompasses the prophylactic treatment of a disease or condition as to prevent or reduce the risk of acquiring or developing a specific disease or condition, or to prevent or reduce the risk of disease/condition recurrence.

The term "administering," "administration" and derivatives thereof refers to the methods that may be used to enable delivery of agents or compositions to the desired site of biological action. These methods include, but are not limited to parenteral administration (e.g., intravenous, subcutaneous, intraperitoneal, intramuscular, intravascular, intrathecal, intranasal, intravitreal, infusion and local injection), transmucosal injection, oral administration, administration as a suppository, and topical administration (e.g., patches, lotions, creams, ointments and the like). One skilled in the art will know of additional methods for administering a therapeutically effective amount of a compound of the present invention for preventing or relieving one or more symptoms associated with a disease or condition.

The term "pharmaceutically acceptable" carrier, diluent, or excipient is a carrier, diluent, or excipient compatible with the other ingredients of the formulation and not deleterious to the recipient thereof.

The term "composition" as used herein is intended to encompass a product comprising the specified ingredients in the specified amounts, as well as any product which results, directly or indirectly, from combination of the specified ingredients in the specified amounts.

The term "hepatotoxicity" or "hepatic toxicity" refers to damage to the liver or impairment of the liver caused by a chemical, drug, or toxic substance. The liver damage causes the organ function improperly.

The term "subject," "individual" or "patient" refers to an animal such as a mammal, including, but not limited to, primates (e.g., humans), cows, sheep, goats, horses, dogs, cats, rabbits, rats, mice and the like.

III. Detailed Descriptions of Embodiments

Provided herein are methods of alleviating fever and/or pain in a subject, e.g., a human subject, who is at risk or suspected of having a risk of hepatotoxicity if administered an acetaminophen monomer drug. The subject may have an increased risk compared to a normal, healthy individual. The methods include administering a pain relieving or fever reducing effective amount of a composition containing an acetaminophen dimer described herein and a pharmaceutically effective carrier or excipient. The method is based, in part, on the discovery that acetaminophen dimers are less likely to induce hepatotoxicity compared to acetaminophen monomers. As such, compositions containing an acetaminophen dimer are advantageous over an acetaminophen monomer, especially for subjects who are at risk of acetaminophen-induced hepatic toxicity.

A. Subjects at Risk of Hepatotoxicity from Administration of an Acetaminophen Monomer Subjects who are at risk of hepatic toxicity if taking an acetaminophen monomer include those with excessive NAPQI production, those with reduced glutathione stores in the body, and those with increased CYP enzyme activity. In some embodiments, reduced glutathione stores is caused by or associated with older age, a restricted diet, underlying liver or kidney disease, or a compromised nutritional status (e.g., from fasting, an eating disorder, cystic fibrosis, gastroenteritis, chronic alcoholism or viral condition). Increased CYP enzyme activity can be associated by, for example, chronic alcohol consumption, smoking tobacco, or drugs such as isoniazid, rifampin, phenytoin, phenobarbital, barbituates, carbamazepine, trimethoprim-sulfamethoxazole, and zidovudine. In some embodiments, a subject at risk of hepatotoxicity carries one or more genetic mutations that predispose the subject to the condition. Alternatively, the subject may have a condition associated with underlying hepatic dysfunction, such as hepatic disease including but not limited to alcoholic liver disease, non-alcoholic liver fatty disease, fatty liver disease, cirrhosis, liver cancer, Gilbert's syndrome, Budd-Chiari syndrome, transthyretin-related hereditary amyloidosis, primary sclerosing cholangitis, fascioliasis and hepatitis.

In some embodiments, subjects, e.g., adult subjects or pediatric subjects at risk of hepatotoxicity include subjects who receive repeated administration of high doses of an acetaminophen monomer, subjects who receive repeated administration of proper therapeutic doses over a shortened time interval, subjects with fever, and subjects with reduced oral intake. In some instances, acetaminophen poisoning or toxicity is caused by repeated misuse, inappropriate dosing, unintentional multiple overdosing, and ingestion of acetaminophen with another hepatotoxic drug.

A subject's risk of hepatotoxicity following ingestion of an acetaminophen monomer can be determined using the Rumack-Matthew nonogram which plots serum concentration of acetaminophen against the time from ingestion. The Rumack-Matthew nonogram is a semi-logarithmic graph with the first time point at 4, hours post injection. Subjects with a serum acetaminophen level lower than the Rumack-Matthew line or treatment line on the nonogram have no or a low risk of hepatotoxicity. On the other hand, subjects with an acetaminophen level higher than the Rumack-Matthew line or treatment line on the nonogram have or a high risk of hepatotoxicity or, have hepatotoxicity. See, e.g., Rumack and Matthew, Pediatrics, 1975, 55(6):871-6.

In some embodiments, a subject at risk of hepatotoxicity has experienced one or more symptoms of hepatotoxicity caused by acetaminophen toxicity. Non-limiting examples of such symptoms include anorexia, nausea, vomiting, malaise, fatigue, pallor and/or diaphoresis at about 0.5 to about 24 hours after acetaminophen ingestion; abdominal pain, abdominal tenderness, liver enlargement, anorexia, nausea, vomiting, tachycardia, hypotension, and/or decreased urinary output at about 18 to about 72 hours after ingestion; and continued nausea, vomiting, abdominal pain, a tender hepatic edge, hepatic necrosis and dysfunction associated with jaundice, coagulopathy, hypoglycemia and hepatic encephalopathy, acute renal failure.

In general, patients most likely to benefit from the compounds or compositions described herein are those whose liver function is compromised, such that drugs that depend upon metabolism for elimination are contra-indicated. Those patients could be someone suffering or recovering from cirrhosis, NASH (non-alcoholic steatohepatitis) where the liver is inflamed and has fat deposits), or even non-alcoholic fatty liver disease similar to NASH. Another category of patients includes those undergoing cancer therapy, such as chemotherapy or radiation therapy. In particular, patients undergoing chemotherapy commonly suffer from general "system-wide" weakness. A further category of patients who would benefit are those with gastrointestinal acidity or gastrointestinal reflux disease (GERD). Because the acetaminophen dimer does not irritate the gastrointestinal mucosa it is be a better alternative than NSAIDS when used for analgesia. The compounds and compositions of the invention can be the analgesic anti-pyretic drug of choice for all these categories of patients.

In some embodiments, a subject receiving the compounds or compositions described herein has been diagnosed or determined to have acetaminophen-induced hepatotoxicity. Such a diagnosis can be made based on results from assays to evaluate, for example, the subject's liver function, kidney function, and acetaminophen levels in serum or plasma. For instance, various clinical tests can be performed including liver function tests such as an alanine aminotransferase (ALT) assay, aspartate aminotransferase (AST) assay, bilirubin assay, and alkaline phosphatase assay; renal function tests such as an electrolytes assay, BUN assay, and creatinine assay; urinalysis; and ECG.

In some embodiments, a subject receiving the compounds or compositions described herein has received N-acetylcysteine (NAC) to treat hepatotoxicity. NAC, an antidote for acetaminophen, can be administered to a subject suffering from hepatotoxicity within 8, hours or more after ingestion acetaminophen. NAC can be administered orally or intravenously.

B. Pharmaceutical Compositions of Acetaminophen Dimers

In certain embodiments, provided herein are pharmaceutical compositions comprising acetaminophen dimers. A pharmaceutical composition can further comprise a pharmaceutically acceptable carrier. Illustrative pharmaceutically acceptable carriers and formulations are described below.

The pharmaceutical compositions also include a barbiturate (e.g., butalbital), opioid e.g., codeine, hydrocodone, oxycodone, tramadol, fentanyl, hydromorphone, meperidine, methadone, and morphine), antihistamine (a $H_1$ antagonist, $H_1$ inverse agonist, $H_2$-antihistamine, $H_3$-antihistamine, $H_4$-antihistamins and the like), caffeine, diphenhydramine, dextromethorphan, pseudoephedrine, derivatives thereof, biosimilar thereof, equivalents thereof, or any combination thereof In some embodiments, the pharmaceutical composition includes 80-95% acetaminophen dimer and 5-20% butalbital. In other embodiments, the pharmaceutical composition includes 70% acetaminophen dimer, 15% butalbital, and 15% caffeine. In some embodiments, the pharmaceutical composition includes 60% acetaminophen dimer, 15% butalbital, 15% caffeine, and 10% codeine. In one embodiment, the pharmaceutical composition contains 85-95% acetaminophen dimer and 5-15% codeine. The composition may contain 90-95% acetaminophen dimer and 5-10% hydrocodone, 90-95% acetaminophen dimer and 5-10% oxycodone, or 90-95% acetaminophen dimer and 5-10% tramadol. The pharmaceutical composition can include 80-90% acetaminophen dimer and 10-20% diphenhydramine. In some instances, the pharmaceutical composition includes 68.5% acetaminophen dimer, 15% diphenhydramine, 7.5% dextromethorphan, and 10% pseudoephedrine.

The pharmaceutical compositions disclosed herein may comprise a pharmaceutically acceptable carrier. In certain aspects, pharmaceutically acceptable carriers are determined in part by the particular composition being administered, as well as by the particular method used to administer the composition. Accordingly, there is a wide variety of suitable formulations of pharmaceutical compositions of the present invention (see, e.g., REMINGTON'S PHARMACEUTICAL SCIENCES, 18TH ED., Mack Publishing Co., Easton, Pa. (1990)).

As will be appreciated, a pharmaceutically acceptable salt of a dimer may be used instead of or in addition to a dimer in any or all of the compositions and methods of treating discussed herein. Thus, in specific embodiments, a pharmaceutically acceptable salt of the dimer (i.e., any pharmaceutically acceptable salt of any of the dimers) is used in the methods of the invention. These salts can be prepared, for example, in situ during the final isolation and purification of the compound or by reacting separately the purified compound in its free base form with a suitable organic or inorganic acid and isolating the salt thus formed. In some embodiments, the pharmaceutically acceptable salt of the dimer is prepared using acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, or p-toluenesulfonic acid. For further description of pharmaceutically acceptable salts that can be used in the methods described herein see, for example, S. M. Berge et al., "Pharmaceutical Salts," 1977, J. Pharm. Sci. 66:1-19, which is incorporated herein by reference in its entirety.

The dimers of the invention can exist in unsolvated as well as solvated forms with pharmaceutically acceptable solvents such as water, ethanol, and the like. In general, the solvated forms are considered equivalent to the unsolvated forms for the purposes of the present invention. In a specific embodiment, the solvated form of the dimer is a hydrate.

In general, salt formation may improve shelf life of the resultant therapeutic agent. Appropriate salt synthesis can afford products that are crystalline, less prone to oxidation and easy to handle. Various salts can be prepared that would afford stable and crystalline compounds. A few examples are hydrochloric, sulfuric, p-toluenesulfonic, methanesulfonic, malonic, fumaric, and ascorbic acid salts.

In certain specific embodiments, such a pharmaceutical composition is formulated as oral tablet or capsule, extended release oral tablet or capsule (hard gelatin capsule, soft gelatin capsule), sublingual tablet or film, extended release sublingual tablet or film, liquid solution, syrup, solution for injection, and transdermal patch. Illustrative pharmaceutically acceptable carriers and formulations are described in more detail below.

C. Dosing and Routes of Administration

The pharmaceutical compositions of the invention are administered in a manner compatible with the dosage formulation, and in such amount as will be therapeutically effective to alleviate fever or pain, e.g., acute or chronic pain. The quantity to be administered depends on a variety of factors including, e.g., the age, body weight, physical activity, and diet of the individual, and the stage or severity of the pain. In certain embodiments, the size of the dose may also be determined by the existence, nature, and extent of any adverse side effects that accompany the administration of a therapeutic agent in a particular individual.

The dimers provided herein can be administered to a subject orally in the conventional form of preparations, such as capsules, microcapsules, tablets, granules, powder, troches, pills, suppositories, oral suspensions, syrups, oral gels, sprays, solutions and emulsions. Suitable formulations can be prepared by methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfate, methylparaben or propylparaben), a stabilizer (e.g., citric acid, sodium citrate or acetic acid), a suspending agent (e.g., methylcellulose, polyvinyl pyrroliclone or aluminum stearate), a dispersing agent (e.g., hydroxypropylmethylcellulose), a diluent (e.g., water), and base wax (e.g., cocoa butter, white petrolatum or polyethylene glycol).

Acetaminophen dimer compounds can be administered transdermally in, for example, a patch. Suitable formulations can be prepared using conventional additives, such as, but not limited to, a penetration or adsorption enhancer, a polymer (e.g., acrylates, polyacrylates, polyalkyl acrylates, polyamides, polyesters, polycarbonates, polyimides, polystyrenes, acrylonitrile butadiene styrene, polyacrylonitrile, polybutadiene, poly(butylene terephthalate), poly(ether sulphone), poly(ether)ketones, polyethylene, poly(ethylene glycol), poly(ethylene teraphthalate), polypropylene, polytetratfluoro ethylene, styrene-acrylonitrile resin, poly(trimethylene terephthalate), polyurethanes, polyvinyl butyral, polyvinylchlorides, polyvinylidenedifluoride, povidones, poly(vinyl pyrrolidone), polychloroprene, fluoroelastomers, chloro-sulphonated rubbers, hypromellose, polyolefine elastomer, polyacrylamide, chlorinated polyethylene, polyethersulphone, nylon, liquid crystal polymers, polyethylene terephthalate (PET), polyphenylsulphone, polypthalaminepolyvinyl alcohol derivatives, poly ethylene glycols, ethylene vinyl acetate, polymethyl methacrylate, cellulose derivatives such as ethyl cellulose, hydroxylpropyl methyl cellulose, sugar derivatives (gums) including derivatives of sorbitol and mannitol, silicone oil and silicone oil derivatives, polysiloxanes including amine-resistant polysiloxanes, and siloxanes), a polymer carrier (e.g., acrylates, povidones and siloxanes), an antioxidant, a filler, and the like. The polymer carrier may also comprise inert carrier components such as, e.g., anti-tacking agents, tackifiers, and plasticizers to achieve appropriate softness, flexibility and tackiness for the polymer carrier to enable the composition to adhere to the surface of skin, and thus provide consistent delivery. Additional descriptions of transdermal formulations are found in, for example, Walters, K A. DERMATOLOGICAL AND TRANSDERMAL FORMULATIONS. Boca Raton: CRC Press, 2002.

Liquid dosage forms can be prepared by dissolving or dispersing the acetaminophen dimer compound and optionally one or more pharmaceutically acceptable adjuvants in a carrier such as, for example, aqueous saline (e.g., 0.9% w/v sodium chloride), aqueous dextrose, glycerol, ethanol, and the like, to form a solution or suspension, e.g., for oral, topical, or intravenous administration. In some embodiments, the liquid dosage form is sterile.

The therapeutically effective dose can also be provided in a lyophilized form. Such dosage forms may include a buffer, e.g., bicarbonate, for reconstitution prior to administration, or the buffer may be included in the lyophilized dosage form for reconstitution with, e.g., water. The lyophilized dosage form may further comprise a suitable vasoconstrictor, e.g., epinephrine. The lyophilized dosage form can be provided in a syringe, optionally packaged in combination with the buffer for reconstitution, such that the reconstituted dosage form can be immediately administered to an individual.

Methods for preparing such dosage forms are known to those skilled in the art (see, e.g., REMINGTON'S PHARMACEUTICAL SCIENCES, 18TH ED., Mack Publishing Co., Easton, Pa. (1990)). The dosage forms typically include a conventional pharmaceutical carrier or excipient and may additionally include other medicinal agents, carriers, adjuvants, diluents, tissue permeation enhancers, solubilizers, and the like. Appropriate excipients can be tailored to the particular dosage form and route of administration by methods well known in the art (see, e.g., REMINGTON'S PHARMACEUTICAL SCIENCES, supra).

Depending on the severity of the subject's pain and the age of the subject, the compounds and compositions of the present disclosure may be administered by oral, parenteral (e.g., intramuscular, intraperitoneal, intravenous, intracerebroventricular, intracisternal injection or infusion, subcutaneous injection, or implant), inhalation, nasal, vaginal, rectal, sublingual, or topical routes of administration. In addition, the compounds and antibodies may be formulated, alone or together, in suitable dosage unit formulations containing conventional nontoxic pharmaceutically acceptable carriers, adjuvants and vehicles appropriate for each rouse of administration. The present disclosure also contemplates administration of the compounds in a depot formulation.

For the treatment of fever or acute or chronic pain, an appropriate dosage level of an acetaminophen dimer will generally be about 0.001 to 100 mg per kg patient body weight per day which can be administered in single or multiple doses. Preferably, the dosage level will be about 0.01 to about 50 mg/kg per day; more preferably about 0.05 to about 10 mg/kg per day. A suitable dosage level may be about 0.01 to 50 mg/kg per day, about 0.05 to 10 mg/kg per day, or about 0.1 to 5 mg/kg per day. Within this range the dosage may be 0.005 to 0.05 mg/kg per day, 0.05 to 0.5 mg/kg per day, 0.5 to 5.0 mg/kg per day, or 5.0 to 50 mg/kg per day.

For oral administration, the acetaminophen dimer can be provided in the form of tablets containing 1.0 to 1000 milligrams of the active ingredient, particularly 1.0 mg, 5.0 mg, 10.0 mg, 15.0 mg, 20.0 mg, 25.0 mg, 50.0 mg, 75.0 mg, 100.0 mg, 150.0 mg, 200.0 mg, 250.0 mg, 300.0 mg, 400.0 mg, 500.0 mg, 600.0 mg, 750.0 mg, 800.0 mg, 900.0 mg, and 1000.0 mg of the active ingredient for the symptomatic adjustment of the dosage to the patient to be treated.

In some embodiments, therapeutically effective amount administered to the subject is about 500 mg to about 1000 mg, e.g., about 500 mg, about 600 mg, about 700 mg, about 800 mg, about 900 mg, or about 1000 mg. In other embodiments, therapeutically effective amount administered to the subject is about 500 mg to about 1000 mg, e.g., about 500 mg to about 900 mg, about 500 mg to about 800 mg, about 500 mg to about 700 mg, about 500 mg to about 600 mg, about 900 mg to about 1000 mg, about 800 mg to about 1000 mg, about 700 mg to about 1000 mg, about 600 mg to about 1000 mg, about 600 mg to about 700 mg, about 700 mg to about 800 mg, or about 800 mg to about 900 mg.

The acetaminophen dimer or composition thereof may be administered 1 to 6 times per day, e.g., 1 time, 2 times, 3 times, 4 times, 5 times or 6 times per day. In other words, the compound can be administered once every 24 hours, once every 12 hours, once every 8 hours, once every 6 hours, or once every 4 hours. Alternatively, the acetaminophen dimer or composition thereof can be administered every 4 to 6 hours or every 6 to 8 hours.

IV. EXAMPLES

The following examples are offered to illustrate, but not to limit the claimed invention.

Example 1

Synthesis of an Acetaminophen Dimer

The compound was synthesized as shown in FIG. 1.
Synthesis of Intermediate 3:

Acetaminophen (1 equiv) and potassium carbonate (4 equiv) in a 3-neck round bottom flask was dissolved in anhydrous DMF (10 vol). The mixture was heated to 60° C. and 1,2-dibromoethane (4 equiv) was added. The reaction mixture was stirred at 60° C. for 16 h and TLC analysis showed consumption of acetaminophen. The mixture was diluted with MTBE, cooled to 10° C., and washed with water. The organic phase was separated, dried over magnesium sulfate, filtered and concentrated. The crude product was purified by silica gel chromatography affording pure product 3. Yield: 65%.

Synthesis of Compound 4:

Compound 3 (1 equiv), acetaminophen (1.2 equiv) and potassium carbonate (3 equiv) was dissolved in anhydrous DMF (10 vol) and the mixture was heated at 60° C. and stirred for 14 hours. TLC analysis showed consumption of intermediate 3. The mixture was diluted with MTBE and washed with water at 15-20° C. The organic phase was separated, dried over magnesium sulfate, filtered and concentrated. The crude product was purified by silica gel chromatography affording pure product 4. Yield: 78%. $^1$H NMR (300 MHz, DMSO-$d_6$): 2.14 (s, 6H, $CH_3$), 4.38 (t, 4H, $CH_2$), 6.80 (d, 4H, Ar), 7.44 (d, 4H, Ar), 9.15 (s, 2H, NH).

Illustrative Pharmaceutical Compositions of an Acetaminophen Dimer

The pharmaceutical composition in Table 1 can be used for oral tablets of the dimers of the invention.

TABLE 1

Pharmaceutical Compositions for Oral Tablets

| Ingredients | % w/w |
|---|---|
| Dimer | 2 |
| Lactose | 83.6 |
| Colloidal Silicon dioxide | 0.67 |
| Microcrystalline cellulose | 10 |
| Croscarmellose sodium | 3.4 |
| Magnesium stearate | 0.33 |

Illustrative Doses of an Acetaminophen Dimer

The dose of the dimers provided herein to be administered to a patient is rather widely variable and can be subject to the judgment of a health-care practitioner. Dosage may be properly varied depending on the age, body weight and medical condition of the subject and the type of administration. In one embodiment, one dose is given per day. In any given case, the amount of the dimer provided herein administered will depend on such factors as the solubility of the active component, the formulation used and the route of administration. By "therapeutically effective dose" we mean a dose that yields an appreciable and beneficial effect in a statistically significant number of patients. In certain embodiments, the patient is a mammal. In more specific embodiments, the patient is a human. In certain specific embodiments, the patient may be a domesticated mammal such as a dog, a cat, or a horse.

Preferred dosages for patients at risk of hepatotoxicity caused by acetaminophen monomers, for example, are from about 500 to about 1000 mg, preferably, from 500 mg to about 800 mg, more preferably about 600 mg for oral administration. Table 2 provides exemplary dosages of dimer according to the invention for a preferred indication, compared to the monomer.

TABLE 2

Dosages of Acetaminophen Dimers

| Monomer | Indication | Dose | Dimer Indication | Dimer dose |
|---|---|---|---|---|
| Acetaminophen | Analgesia | 500 mgs PO | Liver-safe analgesia | 500-1000 mg PO |

The acetaminophen dimers can be combined with one or more additional compounds for use as a sleep aid, antitussive (cough suppressant), analgesic, and cough and cold medicine. Exemplary combinations of the acetaminophen dimer with at least one pharmaceutical compound are provided in Table 3. The percentage of acetaminophen dimer in the combination can be from 50% to 99% of the total. The dose of acetaminophen dimer in the combination can be about 500-1000 mg for oral administration. In some cases, a composition containing 85% acetaminophen dimer and 15% butalbital can be used for pain or fever relief and as a sleep aid. In other cases, a composition containing 85% acetaminophen dimer, 15% butalbital, 15% caffeine and 10% codeine can be used as an antitussive.

TABLE 3

Acetaminophen Dimer Combinations

| Indication or Use | Combination and Proportions |
|---|---|
| Sleep aid | Acetaminophen dimer (85%), butalbital (15%) |
| Antitussive | Acetaminophen dimer (70%), butalbital (15%), caffeine (15%) |
| Antitussive | Acetaminophen dimer (60%), butalbital (15%), caffeine (15%), codeine (10%) |
| Antitussive | Acetaminophen dimer (90%), codeine (10%) |
| Analgesic | Acetaminophen dimer (92.5%), hydrocodone (7.5%) |
| Analgesic | Acetaminophen dimer (95%), oxycodone (5%) |
| Analgesic | Acetaminophen dimer (90%), tramadol (5%) |
| Sleep aid | Acetaminophen dimer (85%), diphenhydramine (15%) |
| Cough and cold aid | Acetaminophen dimer (68.5%), diphenhydramine (15%), dextromethorphan (7.5%), pseudoephedrine (10%) |

Analgesic combinations can be administered as an oral tablet, a liquid solution, a syrup, an injection, or a transdermal patch. Sleep aid combinations or cough and cold aid combinations can be administered as an oral tablet, a liquid solution, or a syrup.

Example 2

In Vitro Assay: Metabolic Stability of Acetaminophen Dimer

Incubations of the acetaminophen dimer described above (e.g., 1 μM) with human liver microsomes (e.g., 1 mg protein/mL) were carried out using a Tecan® Liquid Handling System, or equivalent, at 37±1° C. in 0.2-mL incubation mixtures (final volume) containing potassium phosphate buffer (50, mM, pH 7.4), $MgCl_2$ (3 mM) and EDTA (1 mM, pH 7.4) with cofactor, NADPH-generating system, at the final concentrations indicated in a 96-well plate format. The NADPH-generating system consisted of NADP (1 mM, pH 7.4), glucose-6-phosphate (5 mM, pH 7.4) and glucose-6-phosphate dehydrogenase (1 Unit/mL). The acetaminophen dimer was dissolved in aqueous methanolic solution (methanol 0.5% v/v, or less). Reactions were started typically by addition of the cofactor, and stopped at four designated time points (e.g., up to 60 min) by the addition of an equal volume of stop reagent (e.g., acetonitrile, 0.2 mL containing an internal standard). Zero-time incubations served as 100% value to determine percent loss of substrate.

The samples were subjected to centrifugation (e.g., 920×g for 10 min at 10° C.) and the supernatant fractions analyzed by LC-MS/MS. Additional incubations were carried out with microsomes and a marker substrate (e.g., imipramine, propranol, terfenadine and verapamil) to monitor substrate loss) as a positive control to determine if the test system was metabolically competent.

The above samples were analyzed by an LC-MS/MS method. Analysis was performed for the samples at each incubation solution. Results were determined by a comparison of peak ratios over the time course of the experiment (typically reported as "% Parent Remaining").

Data were calculated with a laboratory information management system such as GALILEO LIMS™ (Thermo Fisher Scientific Inc.) and a reporting tool, e.g., SAP® Crystal Reports®) and the spreadsheet computer program Microsoft® Excel® or an equivalent thereof. The amount of unchanged parent compound was estimated (to determine approximate percent substrate remaining in each incubation) based on analyte/internal standard (IS) peak-area ratios using a LIMS, Analyst® Instrument Control and Data Processing Software (AB SCIEX), or an equivalent thereof.

Figure 2:
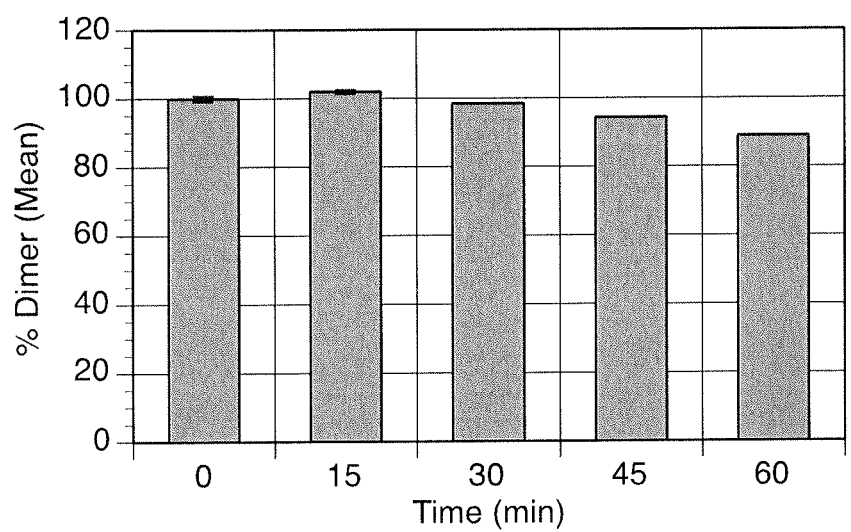
FIG. 2 illustrates the metabolic stability of the acetaminophen dimer.

Results are shown in FIG. 2 and indicate that the acetaminophen dimer was relatively stable in presence of microsomal enzymes for the duration of the assay. The microsomal enzymes are typically responsible for metabolism of drugs such as acetaminophen.

The dimer was stable in presence of the microsomes, with or without the co-factor. The assay was terminated at 1 hour because enzymes are typically not stable beyond 1 hour at incubation temperatures of 37° C.

Example 3

Analgesia—Formalin Paw Mouse Study

Procedure: Male ICR mice weighing 23±3 g were divided into groups of 8 each. All test substances and vehicle control were administered intra-peritoneally in non-fasted mice prior to a sub-planter injection of formalin (0.02 ml 2% solution) administered to one hind paw. The hind paw licking time were recorded for about 35 minutes at 5 min intervals after formalin challenge as a measure of analgesic activity of the test compound. The study design is provided in Table 4. Data is provided in Tables 5 and 6.

TABLE 4

Study Design

| Group | Test Article | Route | Conc ng/ml | Dose ml/kg | Dose mg/kg | Mice (male) |
|---|---|---|---|---|---|---|
| 1 | Vehicle | IP | n/a | 10 | n/a | 8 |
| 2 | Morphine | IP | 0.5 | 10 | 5 | 8 |
| 3 | Acetaminophen | IP | 20 | 10 | 200 | 8 |
| 4 | Acetaminophen dimer (ORP-105) | IP | 40 | 10 | 400 | 8 |
| 5 | Ethylene glycol ether buprenorphine (ORP-107) | IP | 0.5 | 10 | 5 | 8 |

One-way ANOVA followed by Dunnett's test was applied for comparison between vehicle control and test compound treated groups.

TABLE 5

Treatment With Vehicle, Morphine or Acetaminophen Monomer

| Treatment | Route | Dose (mg/kg) | N | B.W. | 0-5 min | 5-10 min | 10-15 min | 15-20 min | 20-25 min | 25-30 min | 30-35 min |
|---|---|---|---|---|---|---|---|---|---|---|---|
| Vehicle (PBS) | IP | 10 mL/kg | 1 | 21 | 103 | 0 | 52 | 86 | 93 | 116 | 72 |
| | | | 2 | 22 | 68 | 0 | 85 | 109 | 69 | 22 | 0 |
| | | | 3 | 21 | 98 | 4 | 0 | 57 | 132 | 55 | 5 |
| | | | 4 | 24 | 78 | 5 | 44 | 88 | 90 | 0 | 11 |
| | | | 5 | 21 | 89 | 18 | 76 | 90 | 130 | 62 | 21 |
| | | | 6 | 21 | 90 | 10 | 27 | 45 | 84 | 4 | 7 |
| | | | 7 | 22 | 140 | 2 | 20 | 125 | 38 | 0 | 0 |
| | | | 8 | 23 | 127 | 14 | 71 | 118 | 131 | 40 | 0 |
| | | | Mean | | 99.1 | 6.6 | 46.9 | 89.8 | 95.9 | 37.4 | 14.5 |
| | | | SEM | | 8.5 | 2.4 | 10.5 | 9.9 | 11.9 | 14.2 | 8.6 |
| Morphine | IP | 5 | 1 | 22 | 11 | 0 | 0 | 0 | 0 | 0 | 0 |
| | | | 2 | 24 | 19 | 0 | 0 | 0 | 3 | 0 | 5 |
| | | | 3 | 22 | 50 | 0 | 0 | 0 | 16 | 112 | 51 |
| | | | 4 | 23 | 5 | 0 | 0 | 0 | 0 | 0 | 0 |
| | | | 5 | 22 | 13 | 0 | 0 | 0 | 0 | 0 | 0 |
| | | | 6 | 24 | 46 | 0 | 57 | 70 | 130 | 76 | 0 |
| | | | 7 | 22 | 1 | 0 | 0 | 0 | 0 | 0 | 0 |
| | | | 8 | 21 | 25 | 0 | 0 | 0 | 0 | 0 | 0 |
| | | | Mean | | 21.3* | 0.0* | 7.1* | 8.8* | 18.6* | 23.5 | 7.0 |
| | | | SEM | | 6.4 | 0.0 | 7.1 | 8.8 | 16.0 | 15.8 | 6.3 |
| | | | % Inhibition | | (79) | (100) | (85) | (90) | (81) | 37 | (52) |
| Acetaminophen | IP | 200 | 1 | 24 | 88 | 0 | 0 | 21 | 0 | 0 | 0 |
| | | | 2 | 23 | 60 | 0 | 0 | 0 | 12 | 2 | 4 |
| | | | 3 | 21 | 79 | 2 | 13 | 78 | 0 | 0 | 0 |
| | | | 4 | 23 | 85 | 0 | 0 | 27 | 103 | 107 | 16 |
| | | | 5 | 23 | 60 | 0 | 0 | 11 | 7 | 0 | 0 |
| | | | 6 | 23 | 59 | 6 | 72 | 118 | 18 | 4 | 0 |
| | | | 7 | 24 | 90 | 0 | 6 | 76 | 70 | 1 | 0 |
| | | | 8 | 24 | 115 | 0 | 13 | 102 | 0 | 0 | 0 |
| | | | Mean | | 79.5 | 1.0* | 13.0* | 54.1 | 26.3* | 14.3 | 2.5 |
| | | | SEM | | 6.9 | 0.8 | 8.7 | 15.8 | 13.7 | 13.3 | 2.0 |
| | | | % Inhibition | | 20 | (85) | (72) | 40 | (73) | (62) | (83) |

TABLE 6

Treatment With Acetaminophen Dimer

| Treatment | Route | Dose (mg/kg) | N | B.W. | 0-5 min | 5-10 min | 10-15 min | 15-20 min | 20-25 min | 25-30 min | 30-35 min |
|---|---|---|---|---|---|---|---|---|---|---|---|
| Acetaminophen dimer (ORP-105) | IP | 400 | 1 | 22 | 14 | 0 | 0 | 0 | 20 | 24 | 62 |
| | | | 2 | 25 | 21 | 0 | 0 | 0 | 9 | 17 | 30 |
| | | | 3 | 25 | 10 | 0 | 0 | 0 | 0 | 0 | 0 |
| | | | 4 | 24 | 20 | 0 | 0 | 0 | 0 | 3 | 4 |
| | | | 5 | 22 | 20 | 0 | 0 | 0 | 11 | 102 | 91 |
| | | | 6 | 22 | 8 | 0 | 0 | 0 | 0 | 0 | 0 |
| | | | 7 | 25 | 9 | 0 | 0 | 0 | 50 | 74 | 67 |
| | | | 8 | 22 | 6 | 0 | 0 | 0 | 0 | 0 | 3 |
| | | | Mean | | 13.5* | 0.0* | 0.0* | 0.0* | 11.3* | 27.5 | 32.1 |
| | | | SEM | | 2.2 | 0.0 | 0.0 | 0.0 | 6.1 | 13.8 | 12.9 |
| | | | % Inhibition | | (86) | (100) | (100) | (100) | (88) | 26 | 0 |
| Bupromorphine (ORP-107) | IP | 5 | 1 | 22 | 98 | 8 | 56 | 126 | 191 | 190 | 121 |
| | | | 2 | 23 | 96 | 0 | 5 | 17 | 28 | 25 | 2 |
| | | | 3 | 22 | 75 | 2 | 0 | 6 | 141 | 176 | 170 |
| | | | 4 | 22 | 43 | 1 | 0 | 7 | 46 | 90 | 24 |
| | | | 5 | 23 | 26 | 0 | 0 | 91 | 102 | 91 | 2 |
| | | | 6 | 23 | 38 | 0 | 64 | 194 | 195 | 168 | 69 |
| | | | 7 | 22 | 84 | 1 | 1 | 68 | 93 | 105 | 0 |
| | | | 8 | 25 | 34 | 0 | 5 | 103 | 177 | 155 | 82 |
| | | | Mean | | 61.8* | 1.5* | 16.4* | 76.5 | 121.6 | 125.0* | 58.8 |
| | | | SEM | | 10.5 | 1.0 | 9.6 | 23.4 | 22.9 | 20.0 | 22.4 |
| | | | % Inhibition | | 38 | (77) | (65) | 15 | 0 | 0 | 0 |

Header spans: Hind Paw Licking Time (Seconds) / Time (Minutes)

Figure 3:
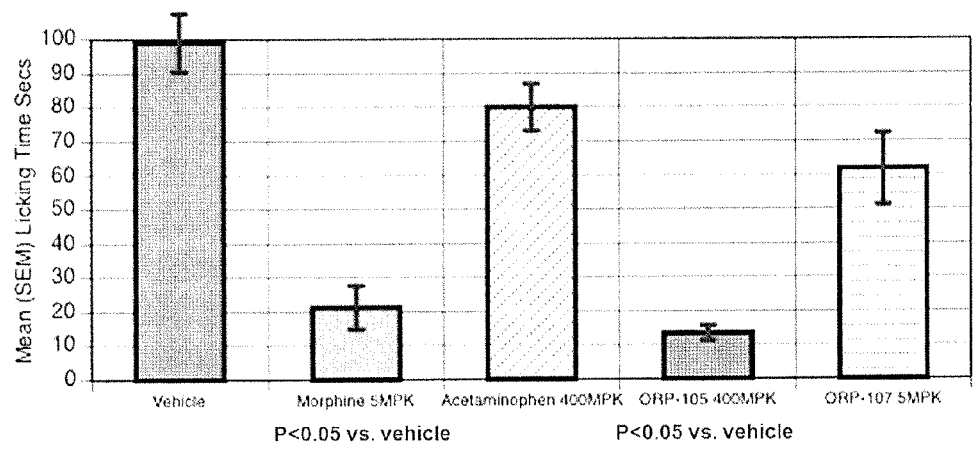
FIG. 3 illustrates the analgesic effect of the acetaminophen dimer in a formalin paw study.

FIG. 3 shows the analgesic effect of the acetaminophen dimer (ORP-105) in comparison to vehicle, morphine, acetaminophen monomer and ethylene glycol ether buprenorphine. The mice receiving acetaminophen dimer had the shortest mean licking time compared to those receiving the other treatments. The results show that acetaminophen dimer is an effective analgesic. Its effect is rapid and greater than 2× that of acetaminophen monomer. The analgesic effect of the acetaminophen dimer is similar to that of morphine. The data show that administration of acetaminophen dimer can relieve pain including acute nociception such as in the immediate c-fiber mediated phase, and sensitization which occurs in the second phase.

It is understood that the examples and embodiments described herein are for illustrative purposes only and that various modifications or changes in light thereof will be suggested to persons skilled in the art and are to be included within the spirit and purview of this application and scope of the appended claims. To the extent there is conflict between the priority applications and the present application, any inconsistencies are to be resolved in favor of the present application. All publications and patents cited herein are hereby incorporated by reference in their entirety for all purposes.

What is claimed is:

1. A method of treating pain in a patient suffering from cirrhosis, liver cancer, hepatitis, alcoholic liver disease, non-alcoholic fatty liver disease, primary sclerosing cholangitis, Gilbert's syndrome, Budd-Chiari syndrome, transthyretin-related hereditary amyloidosis or acetaminophen poisoning, the method comprises administering to the patient a therapeutically effective amount of a pharmaceutical composition comprising a pharmaceutically acceptable carrier or excipient and an acetaminophen dimer compound having Formula (1):

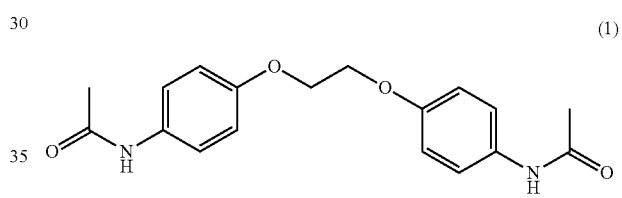

(1)

or a pharmaceutically acceptable salt or solvate thereof.

2. The method of claim 1, wherein the patient is an adult human patient.

3. The method of claim 1, wherein the pharmaceutical composition further comprises a barbiturate, opioid, antihistamine, caffeine, diphenhydramine, dextromethorphan, pseudoephedrine or any combination thereof.

4. The method of claim 1, wherein the pharmaceutical composition is administrated orally, rectally, sublingually, subcutaneously, intramuscularly, intravenously, transdermally, or transmucosally.

5. The method of claim 1, wherein the therapeutically effective amount administered is about 500 mg to about 1000 mg.

6. The method of claim 5, wherein the pharmaceutical composition is formulated as an oral tablet or extended release oral tablet.

7. The method of claim 1, wherein the patient suffers from cirrhosis.

8. The method of claim 1, wherein the patient suffers from liver cancer.

9. The method of claim 1, wherein the patient suffers from hepatitis.

10. The method of claim 1, wherein the patient suffers from alcoholic liver disease.

11. The method of claim 1, wherein the patient suffers from non-alcoholic fatty liver disease.

12. The method of claim 1, wherein the patient suffers from primary sclerosing cholangitis.

13. The method of claim 1, wherein the patient suffers from acetaminophen poisoning.

* * * * *